United States Patent
Mooney et al.

(10) Patent No.: US 11,304,827 B2
(45) Date of Patent: Apr. 19, 2022

(54) UNIDIRECTIONAL ACTUATED EXOSKELETON DEVICE

(71) Applicant: Dephy, Inc., Maynard, MA (US)

(72) Inventors: Luke Mooney, Sudbury, MA (US); Jean-Francois Duval, Belmont, MA (US)

(73) Assignee: Dephy, Inc., Maynard, MA (US)

( * ) Notice: Subject to any disclaimer, the term of this patent is extended or adjusted under 35 U.S.C. 154(b) by 285 days.

(21) Appl. No.: 16/295,472

(22) Filed: Mar. 7, 2019

(65) Prior Publication Data
US 2020/0022821 A1 Jan. 23, 2020

Related U.S. Application Data

(62) Division of application No. 15/782,306, filed on Oct. 12, 2017, now Pat. No. 10,265,195.

(Continued)

(51) Int. Cl.
*A61H 1/02* (2006.01)
*A61F 5/01* (2006.01)
(Continued)

(52) U.S. Cl.
CPC .............. *A61F 2/6607* (2013.01); *A61F 2/70* (2013.01); *A61F 5/01* (2013.01); *A61H 1/024* (2013.01);
(Continued)

(58) Field of Classification Search
CPC ........ A61F 5/01; A61F 5/0102; A61F 5/0111; A61F 5/0113; A61F 5/0116;
(Continued)

(56) References Cited

U.S. PATENT DOCUMENTS 5,056,509 A * 10/1991 Swearington ......... A61F 5/0127
602/29
5,317,820 A * 6/1994 Bell ........................ A43B 5/00
36/114
(Continued)

FOREIGN PATENT DOCUMENTS

JP 2007089633 A 4/2007
JP 2011092507 A 5/2011
(Continued)

OTHER PUBLICATIONS

Mooney and Herr; Journal of NeuroEngineering and Rehabilitation (2016) 13:4; "Biomechanical walking mechanisms underlying the metabolic reduction caused by an autonomous exoskeleton", pp. 1-12; Published Jan. 28, 2016.
(Continued)

*Primary Examiner* — Ophelia A Hawthorne
(74) *Attorney, Agent, or Firm* — Barlow, Josephs & Holmes, Ltd.; David R. Josephs (57) ABSTRACT

The present invention is directed to an autonomous exoskeleton device that includes one or more actuators, one or more controllers, one or more sensors with one or more unidirectional transmissions. The present invention provides a mechanical joint in parallel with a biological joint. The exoskeleton device preferably includes and electric motor and winch, chain, belt, cam transmission or other mechanism for providing unidirectional force to assist rotation about the biologic joint. Moreover, a controller, a motor angle sensor, joint angle sensor and/or force sensor may be used for additional control and monitoring of the device. The motor may be any type of motor, but is preferably brushless in configuration where its diameter is larger than its length to provide a compact and lightweight exoskeleton device.

13 Claims, 8 Drawing Sheets

Related U.S. Application Data (60) Provisional application No. 62/407,671, filed on Oct. 13, 2016, provisional application No. 62/433,357, filed on Dec. 13, 2016.

(51) Int. Cl.
  *A61F 2/66* (2006.01)
  *A61F 2/70* (2006.01)
  *A61H 3/00* (2006.01)
  *A61B 5/00* (2006.01)
  *A61F 2/50* (2006.01)
  *A61F 2/60* (2006.01)

(52) U.S. Cl.
  CPC ......... *A61H 1/0262* (2013.01); *A61H 1/0266* (2013.01); *A61H 3/00* (2013.01); *A61B 5/4528* (2013.01); *A61F 2002/503* (2013.01); *A61F 2002/607* (2013.01); *A61F 2002/701* (2013.01); *A61H 2003/007* (2013.01); *A61H 2201/0134* (2013.01); *A61H 2201/0192* (2013.01); *A61H 2201/1215* (2013.01); *A61H 2201/14* (2013.01); *A61H 2201/1418* (2013.01); *A61H 2201/1642* (2013.01); *A61H 2201/1671* (2013.01); *A61H 2201/1676* (2013.01); *A61H 2201/50* (2013.01); *A61H 2201/5058* (2013.01); *A61H 2201/5061* (2013.01); *A61H 2201/5069* (2013.01); *A61H 2201/5097* (2013.01); *A61H 2205/10* (2013.01); *A61H 2205/102* (2013.01)

(58) Field of Classification Search
  CPC ...... A61F 5/0127; A61F 5/019; A61F 5/0195; A61F 5/14; A61F 2005/0155; A61F 13/06; A61F 13/064; A61F 13/066; A61F 13/067; A43B 7/1495; A43B 7/18; A43B 7/19; A43B 7/20; A43B 7/28
  See application file for complete search history.

(56) References Cited

U.S. PATENT DOCUMENTS

| | | | |
|---|---|---|---|
| 5,363,025 A | 11/1994 | Colling | |
| 7,513,880 B2 * | 4/2009 | Ingimundarson | A43B 13/026 602/23 |
| 8,235,924 B2 | 8/2012 | Bachmann et al. | |
| 8,516,918 B2 | 8/2013 | Jacobsen et al. | |
| 8,702,811 B2 | 4/2014 | Ragnarsdottir et al. | |
| 8,731,716 B2 | 5/2014 | Jacobsen et al. | |
| 8,771,370 B2 | 7/2014 | Albrecht-Laatsch et al. | |
| 8,852,292 B2 | 10/2014 | Ragnarsdottir et al. | |
| 8,894,592 B2 | 11/2014 | Amundson et al. | |
| 9,445,931 B2 | 9/2016 | Imaida et al. | |
| 2006/0211966 A1 | 9/2006 | Hatton et al. | |
| 2009/0216167 A1 * | 8/2009 | Harris | A61F 5/0127 602/27 |
| 2009/0222105 A1 | 9/2009 | Clausen | |
| 2010/0076360 A1 | 3/2010 | Shimada et al. | |
| 2010/0130893 A1 | 5/2010 | Sankai | |
| 2010/0256538 A1 | 10/2010 | Ikeuchi | |
| 2010/0262044 A1 * | 10/2010 | Siegler | A61H 3/00 600/592 |
| 2012/0143112 A1 * | 6/2012 | Tomiyama | A61F 5/0125 602/27 |
| 2012/0255194 A1 * | 10/2012 | Schwartz | A61F 5/0127 36/19.5 |
| 2012/0271207 A1 * | 10/2012 | Schoen | A61F 5/0102 601/34 |
| 2012/0283845 A1 | 11/2012 | Herr et al. | |
| 2013/0012852 A1 | 1/2013 | Imaida et al. | |
| 2013/0102934 A1 | 4/2013 | Ikeuchi | |
| 2013/0226059 A1 * | 8/2013 | Morris | A61F 5/0127 602/27 |
| 2014/0330431 A1 | 11/2014 | Hollander et al. | |
| 2015/0173993 A1 | 6/2015 | Walsh et al. | |
| 2015/0190249 A1 | 7/2015 | Ishibashi et al. | |
| 2015/0196450 A1 * | 7/2015 | Lee | A61H 1/0244 602/16 |
| 2015/0209214 A1 | 7/2015 | Herr et al. | |
| 2015/0374573 A1 | 12/2015 | Horst et al. | |
| 2016/0220407 A1 * | 8/2016 | Jordan | A61F 5/0113 |
| 2016/0331557 A1 | 11/2016 | Tong et al. | |

FOREIGN PATENT DOCUMENTS

| | | | |
|---|---|---|---|
| JP | 201390693 A | 5/2013 | |
| JP | 5316708 B2 | 7/2013 | |
| WO | 2010091377 A2 | 8/2010 | |
| WO | 2014151584 A1 | 9/2014 | |
| WO | 2016164395 A2 | 10/2016 | |

OTHER PUBLICATIONS

Mooney et al., Journal of Neuroengineering and Rehabilitation 2014, 11:151; "Autonomous exoskeleton reduces metabolic cost of human walking"; Published Nov. 3, 2014.

* cited by examiner

UNIDIRECTIONAL ACTUATED EXOSKELETON DEVICE

CROSS-REFERENCE TO RELATED APPLICATION

This patent document is a divisional of U.S. patent application Ser. No. 15/782,306, filed on Oct. 12, 2017, which claims priority to earlier filed U.S. Provisional Patent Application No. 62/407,671, filed on Oct. 13, 2016, and U.S. Provisional Patent Application No. 62/433,357, filed on Dec. 13, 2016, the entire contents of which are incorporated herein by reference.

GOVERNMENT SUPPORT

This invention was made with government support under W911QY-16-C-0072 from the United States Army.

BACKGROUND OF THE INVENTION

The invention relates generally to an exoskeleton, a device worn by a person to augment physical abilities. Exoskeletons can be considered passive or active. Passive devices do not require an energy source, such as a battery. Active devices require an energy source to power electronics and usually one or many actuators. It is desirable for exoskeletons to be as lightweight as possible, since the user must carry and move the device along with the body. It is also desirable for these devices to be capable of providing large amounts of force, torque and/or power to the human body in order to assist with motion. These two requirements of low mass and high force/torque/power are often competing requirements and design tradeoffs must be made. Furthermore, it is difficult to apply large forces and torques to the human body. The musculoskeletal system of the human body is capable of sustaining incredible amounts of torque and force, but the exterior of the body is not accustomed to withstanding similar magnitudes of force/torque. Along with being lightweight, and capable of producing high forces/torques/powers, exoskeletons should also be comfortable and efficient at transferring energy to the human. Furthermore, the device should not interfere with the natural range of motion of the body.

It is also desirable for active exoskeletons to be energy efficient and easily controlled. Active exoskeletons require an energy source to power electronics, sensors and usually actuators. Typically, batteries are used with electric motors. However, compressed air can also be used to power pneumatic exoskeletons. The exoskeleton should be as efficient as possible at converting the energy source into useful mechanical force/torque/power. Since the user is often required to also carry the energy source, an efficient device results in a lighter device, a primary design objective. Onboard electronics allow designers to control the exoskeleton, but the device can be mechanically designed to allow for easier control. For example, active devices with a lower transmission ratio are often easier to control and back drive. Output force and torque sensors can also be used to make controlling easier.

SUMMARY OF THE INVENTION

The present invention preserves the advantages of prior art exoskeleton devices. In addition, it provides new advantages not found in currently available exoskeleton devices and overcomes many disadvantages of such currently available exoskeleton devices.

The invention is generally directed to the novel and unique exoskeleton designs that address the problems associated with known exoskeleton devices relating to design challenges of device mass, force/torque/power output, comfort, efficiency and controllability, and the like.

The present invention provides an autonomous exoskeleton that includes one or more actuators, one or more controllers, one or more sensors with one or more unidirectional transmissions. The present invention also provides a mechanical joint in parallel with a biological joint. The exoskeleton device preferably includes an electric motor and a winch, chain, belt, cam transmission or other mechanism for providing unidirectional force. Moreover, a controller, a motor angle sensor, joint angle sensor and/or force sensor may be provided. The motor may be any type of motor, but is preferably brushless in configuration where its diameter is larger than its length.

It is therefore an object of the present invention to provide a new and novel exoskeleton device that is compact, lightweight and inexpensive to manufacture yet is powerful and easy to control to address the problems associated with prior art exoskeleton devices.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE INVENTION

Figure 1:
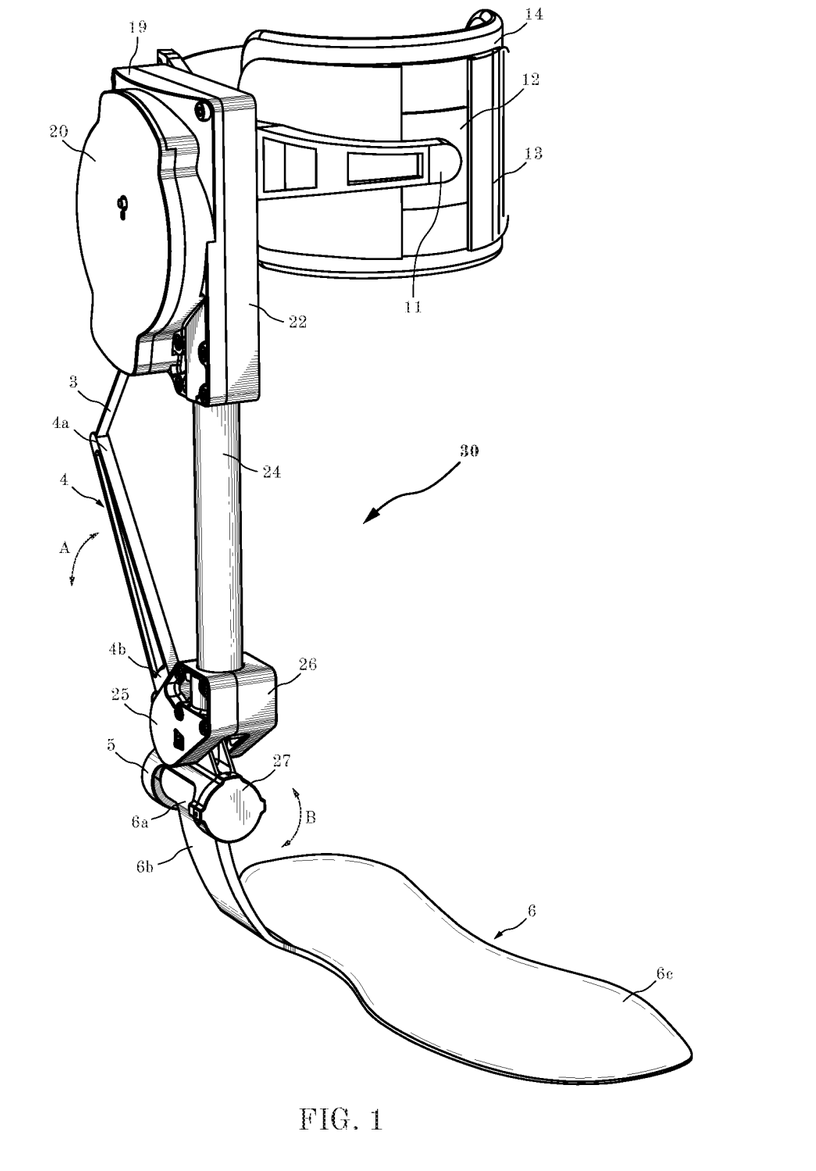
FIG. 1 is a perspective view of the exoskeleton device of the present invention.
Figure 2:
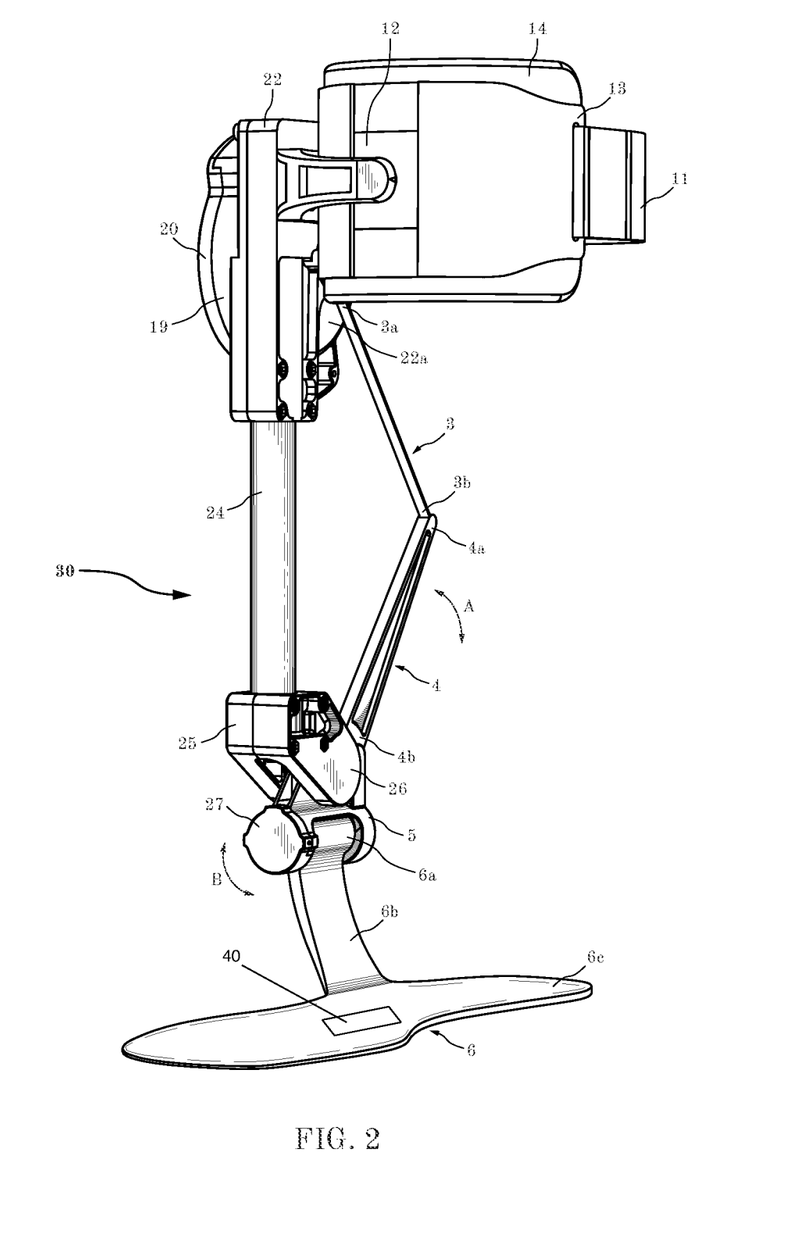
FIG. 2 is a reverse perspective view of the exoskeleton device of the present invention of FIG. 1.
Figure 3:
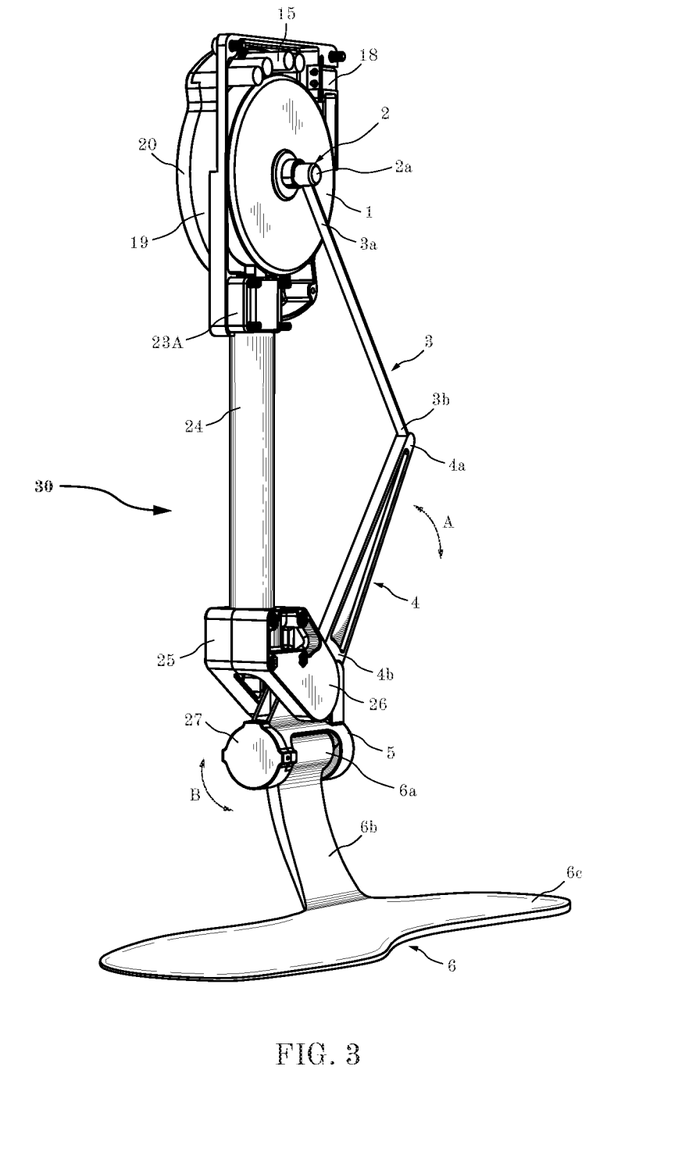
FIG. 3 is the reverse perspective view of the exoskeleton device of the present invention of FIG. 1 with various components removed for illustration purposes to show attachment of the drive belt to the drive spool at an ankle joint.
Figure 7:
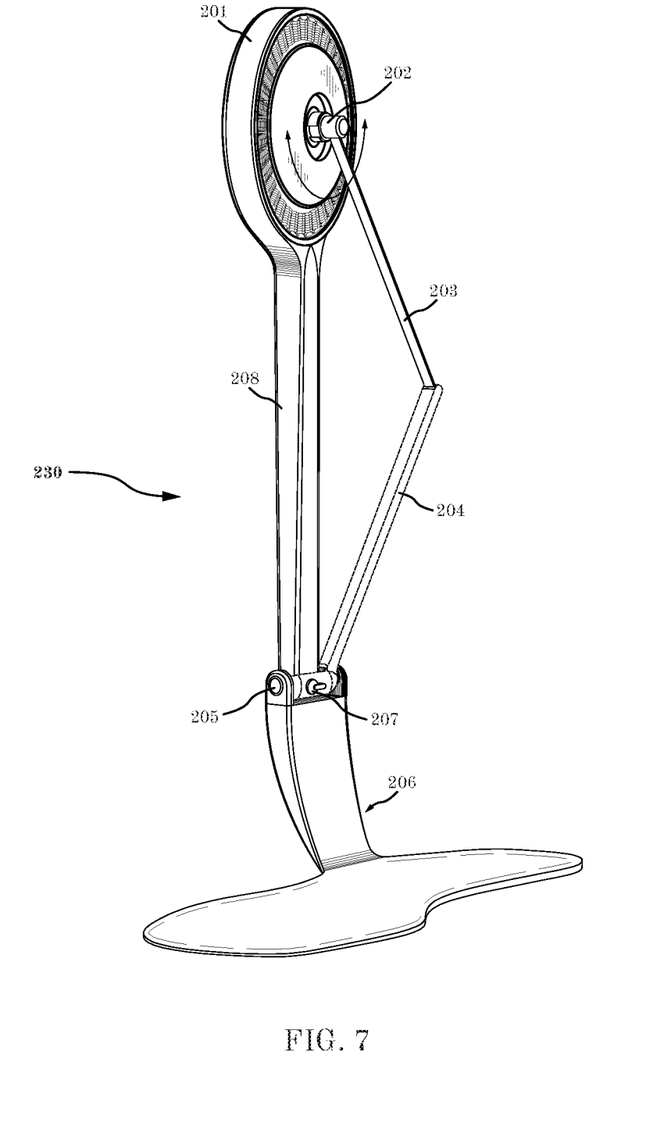
FIG. 7 is a reverse perspective view of the exoskeleton device of the present invention of FIG. 1 with various components removed for illustration purposes to show the motor that drives the drive spool.

Referring first to FIGS. 1-4 and 7, details of the exoskeleton 30 of the present invention is shown. FIGS. 1 and 2 show two different perspective views of the exoskeleton 30 from the outside. Details of the different components is shown in FIGS. 3 and 7 where various components are removed for illustration purposes.

Referring to FIGS. 1 and 2, the exoskeleton 30 generally shows a shank tube 24 with a medial ankle joint bearing housing 26 located on the lower end and a medial actuator housing 22 located at the top thereof. As will be discussed in connection with FIG. 2, a motor 1, resides in lateral actuator housing 19 that includes a control electronics cover 20 thereon. Attached to the medial actuator housing 22 is a calf attachment 11 to secure the upper portion of the exoskeleton to a calf portion of the user's leg. Details of such attachment is shown in connection with FIGS. 5A-5C and 6A-6C below. The calf attachment 11 preferably includes a shin slide 12 and a shin guard 13 as well as a shin pad 14 for additional custom adjustment for better cushioning and comfort for the user. The components of the calf attachment may be adjusted, as is well known in the art, to provide a tight but not constricting fit.

As a result, this attachment to the upper leg of the user transfers normal forces to the anterior part of the leg, is lightweight, easy and quick to secure and adjust, can adapt to many leg sizes and shapes, has minimal bulk to avoid interference with other pieces of equipment, does not limit range of motion (minimal medial, anterior and posterior protrusions), can be used over pants and is comfortable to the user.

The medial ankle joint bearing housing 26 includes a lateral ankle joint bearing housing 25 the pivotally receives ankle joint cross member 5 therein. The free end of the lever arm 4 is fixed to the joint cross member 5. Therefore, dorsiflexion motion of an ankle joint causes the ankle joint lever arm 4 to move accordingly, namely in the direction A shown in FIG. 2. A composite footplate, generally referenced as 6, has a number of components. The footplate can be generally made of a material selected from the group consisting of unidirectional carbon fiber, twill weave carbon fiber, and/or plain weave carbon fiber. In some embodiments, the footplate can be made of a composite material with fibers extending in a plurality of orientations and the footplate can be flexible at a metatarsal joint. It includes a socket portion 6a, a vertical connector portion 6b and composite shank 6c. Eversion and inversion of an ankle joint is permitted by the pivoting action of the rounded free end 6a of composite footplate 6 within ankle joint cross member 5 in a cylindrical shaft and socket type pivoting interconnection 6a, namely in direction B shown in FIGS. 1 and 2. In some embodiments, the footplate 6 can include one or more embedded sensors 40, shown generally as a black box without regard for the exact location with respect to the footplate in FIG. 2, the embedded sensors can be selected from the group consisting of force sensors, pressure sensors, strain sensors, IMU sensor, humidity or liquid sensor, and temperature sensors.

A lower free end 4b of lever arm 4 is fixed connected to the ankle joint cross member 5 while the upper free end 4a of the lever arm 4 is connected to drive belt 3. The lever arm 4 is preferably angled upwards at a 50-degree angle so that it does not protrude beyond the vertical plane at the back of the heel. This angling also improves the variable transmission profile.

The drive belt 3 is wound up and unwound about a drive spool 2 driven by motor 1, as shown in FIG. 3, which has medial actuator housing 22 removed for illustration purposes. With the housing 22 removed in FIG. 3, control electronics 15 and power jack 18 may be seen residing therein.

Figure 4:
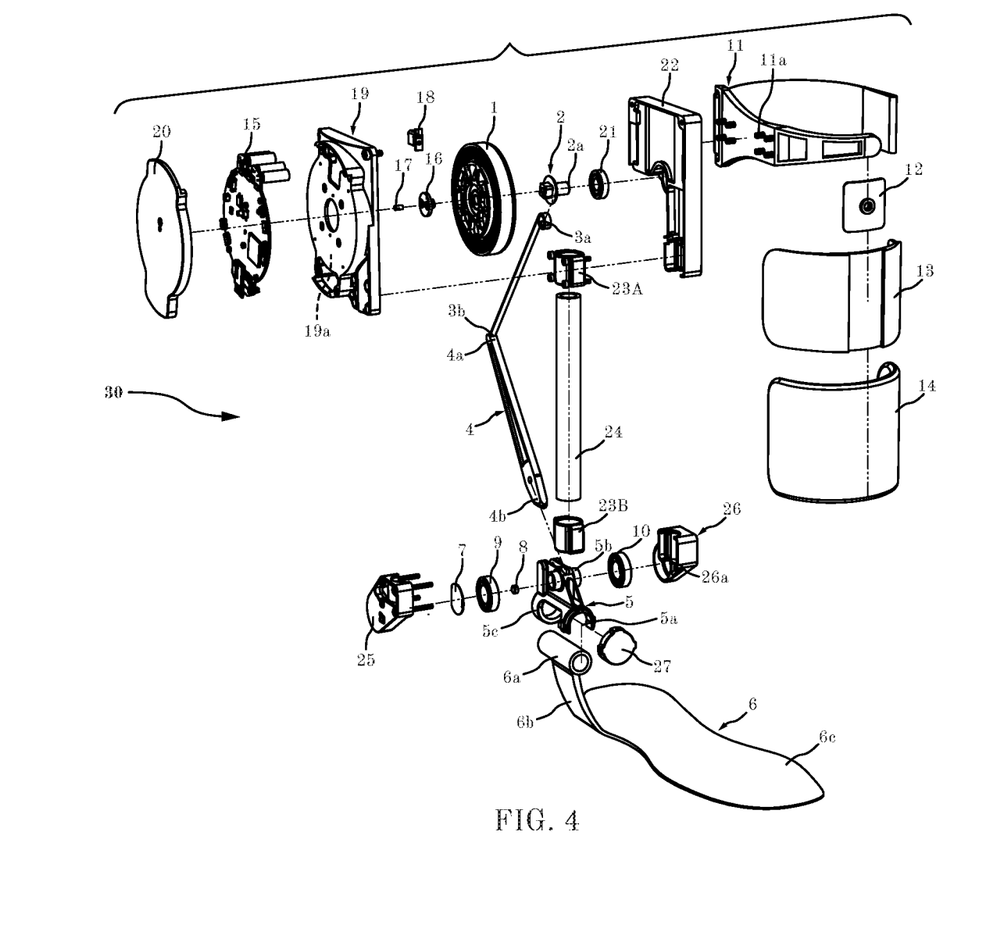
FIG. 4 is an exploded perspective view of the exoskeleton device of the present invention of FIG. 1.

Referring now to FIG. 4, an exploded view of the exoskeleton 30 of the present invention is shown. The ankle motor 1 is mounted between the medial actuator housing 22 and the lateral actuator housing 19, namely, within seat 19a of lateral actuator housing 19. Control electronics 15 are mounted to the exterior surface of the lateral actuator housing 19 and cover 20 is affixed thereon. A motor angle sensor magnet mount 16 is provided to carry motor angle sensor magnet 17. The power jack 18 is mounted to the lateral actuator housing 19 as well. Drive spool 2 is fixed to motor 1 so that rotation of motor 1 rotates the drive spool 2. A medial motor bearing 21 is also provided between the spool 2 and medial actuator housing 22 for improved smooth operation. The free end 2a extends clear of inner face 22a of the medial actuator housing with the free end 3a of drive belt 3 affixed thereto. Thus, as will be described below, rotation of drive spool 2 causes the drive belt 3 to be wound and out as it is being wrapped and unwrapped from about the drive spool 2. The configuration of the drive spool 2 may be modified, as needed. For example, the diameter, length, profile and eccentricity of the drive spool 2 may be modified, as needed to achieve the required winding and unwinding action of the drive belt 3.

The calf attachment 11 is fastened to the medial actuator housing 22 by fasteners 11a. The cushioning shin pad 14, shin guard 13 and shin slide 12 are adjustably interconnected with one another to secure the upper portion of the exoskeleton 30 to the user's body, such as a leg calf. Other structures and configurations may alternatively be used to secure the exoskeleton 30, as desired.

Still referring to FIG. 4, the shank tube 24 includes an upper shank tube ferrule 23A to enable it to be mounted between the lateral actuator housing 19 and medial actuator housing 22. A bottom shank tube ferrule 23B enables the lower portion of the shank tube 24 to be secured between the lateral ankle joint bearing housing 25 and medial ankle joint bearing housing 26.

The ankle joint cross 5 includes a bottom socket 5c and a pivot member 5b at the top thereof. While the shank tube 24 is fixed to the lateral ankle joint bearing housing 25 and medial ankle joint bearing housing 26, the ankle joint cross 5 is pivotally connected to the lateral ankle joint bearing housing 25 and medial ankle joint bearing housing 26 wherein pivot boss 5b sits within seat 26a of joint bearing housing 26 via a medial ankle joint bearing 10. On the opposing side, another pivot boss 5c is provides that pivotally communicates with lateral ankle joint bearing housing via lateral ankle joint bearing 9. An ankle angle joint sensor 7 and ankle angle joint sensor magnet 8 are provided to sense rotational movement of ankle lever arm 4 relative to the shank tube 24 and the user's calf position.

The ankle joint cross also includes a socket 5a to pivotally receive cylinder 6a of composite footplate 6, which also include a connector member 6b and composite shank 6c that may receive a sole of footwear or may be incorporated directly into a sole of footwear (not shown in FIG. 4). Ankle joint cross cap 27 is provided on the free end thereof. As discussed in FIGS. 1 and 2 above, such a cylinder and socket configuration permits eversion and inversion of the ankle joint. Further details of such capability are shown in FIGS. 5A-5C where eversion and inversion movement of the ankle joint and, in turn, eversion and inversion movement of the footwear 32 is permitted due to the cylinder and socket arrangement movement in the direction of the arrows shown.

FIG. 7, which has many components removed for illustration purposes, shows an alternative embodiment 230 of an exoskeleton in accordance with the present invention. For example, the eversion and inversion rotary joint 205 that rotates relative to footplate 206 may be configured as a forked joint where footplate 206 receives a free end of shank 208 with a sensor 207. An ankle motor 201 may be incorporated into the opposing free end of the shank 208 to provide the rotating drive spool 202. The lever arm 204 may be pivotally connected to a region of the footplate to provide the desired direction of rotation with movement of the body joint where the drive belt 203 is wound and unwound from drive spool 202.

Figure 8:
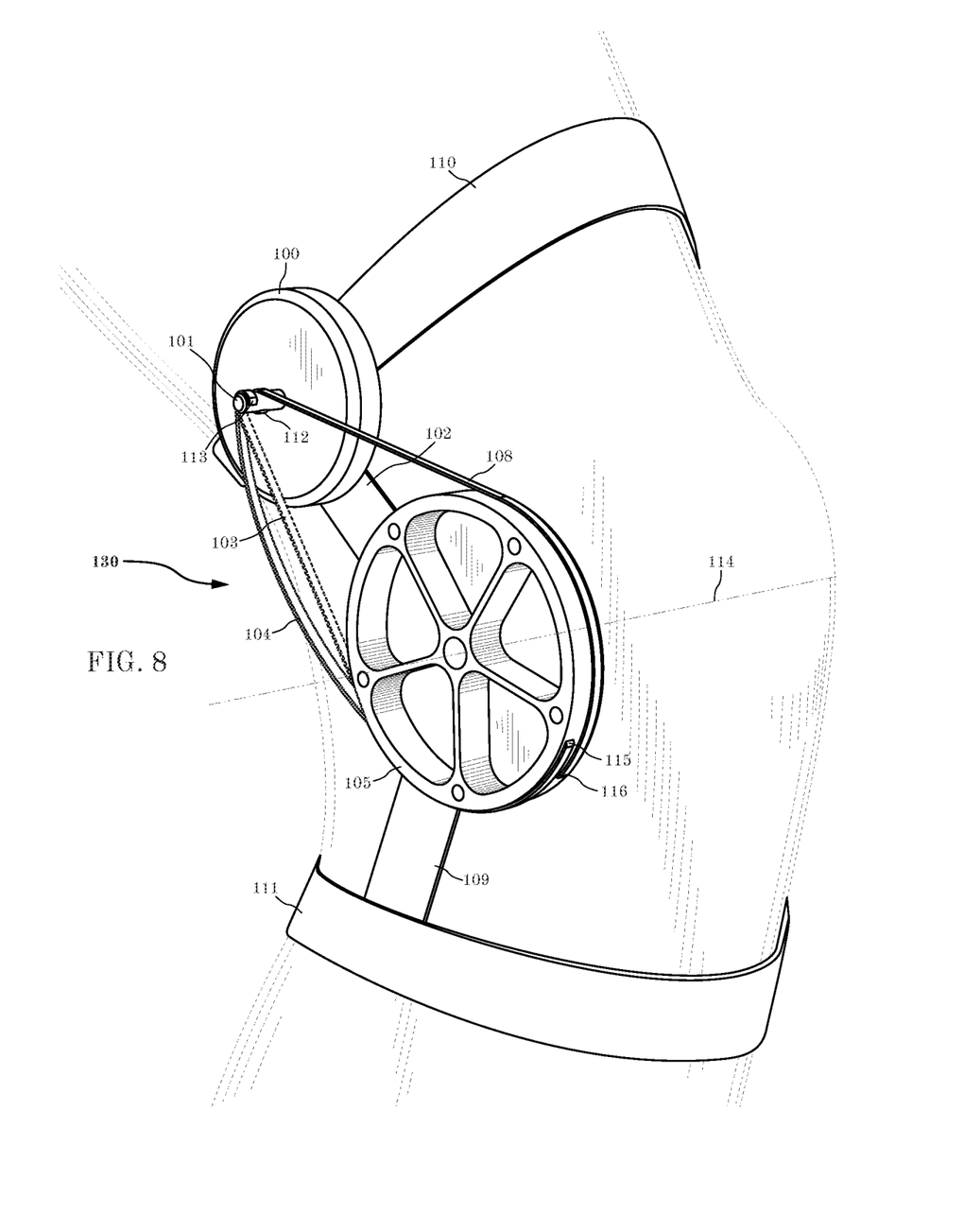
FIG. 8 is a perspective view of an alternative embodiment of the exoskeleton device of the present invention used at a knee joint.

FIG. 8 shows a further alternative embodiment of the present invention that provides an exoskeleton that is adapted for use at a knee joint. A motor 100 is provided with a drive spool 101 is secured to the user by a thigh attachment 110 and a shank attachment 111. Rigid shank housing 109 is connected to the shank attachment 111 where the shank housing 109 pivotally connects to joint pulley 105 which is co-axial with the rotation axis 114 of the knee joint. Rigid thigh housing 102 pivotally connects the motor 100 to the joint pulley 105. A knee flexion belt 104 is provided which is connected to the drive spool 101 at 113 and to the joint pulley at 115. A knee extension belt is 108 also provided, which is connected to the drive spool at 112 and to the joint pulley at 116. When the knee extension belt 108 is engaged, the knee flexion belt 104 exhibits slack. When the knee extension belt 108 is disengaged and slack, the knee flexion belt 103, becomes engaged, as shown in broken lines. Thus, in this embodiment, dual unidirectional control in the extension and flexion directions can be achieved.

Figure 5A:
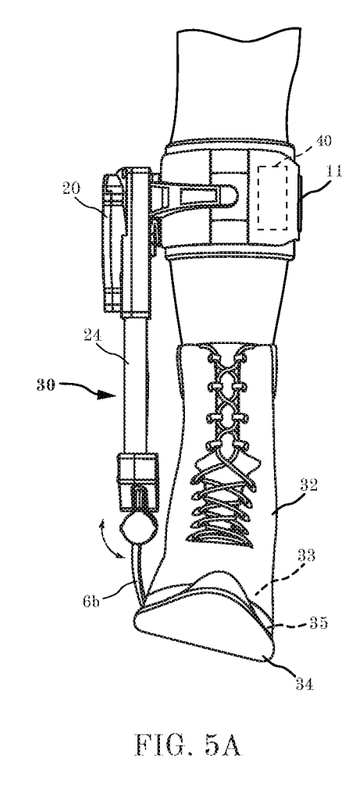
FIG. 5A-5C show front views of the exoskeleton device of the present invention with different degrees of eversion and inversion of the ankle joint.
Figure 5B:
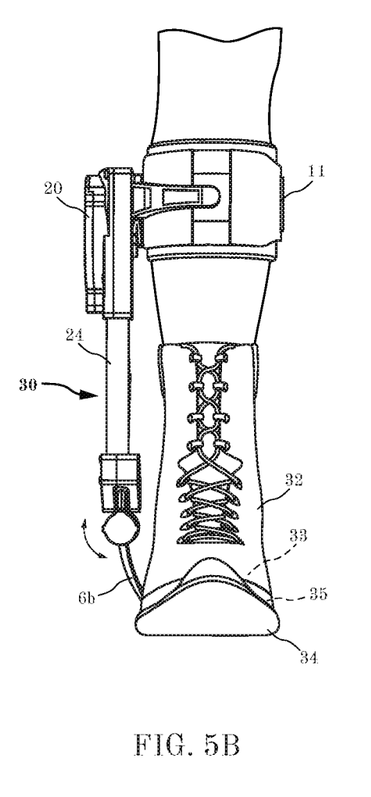
Figure 5C:
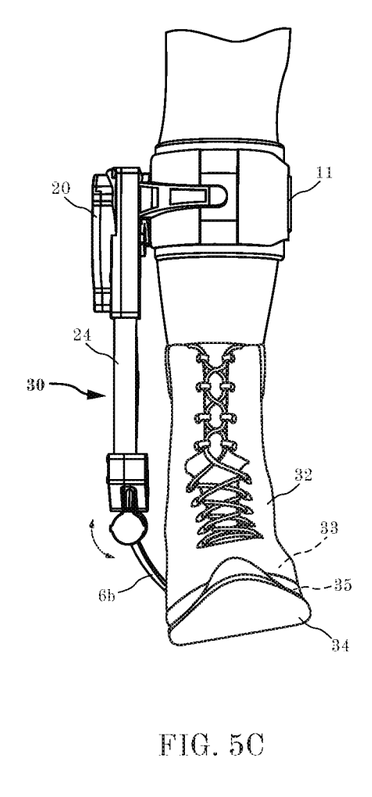

In accordance with the present invention, in operation and use that can best be seen in FIGS. 5A-5B, calf attachment 11 attaches to the shin 210 of the leg 212 of a user as described above to secure to a rigid structure, such as the shank tube 24, located on the lateral side of the leg 212. An integrated strain gage (or any other force sensor) may be provided to measure the force applied to the leg 212. The joint structure shown in detail in FIGS. 1-3 and 4 can be a simple rotary joint or a more complex combination of joints such as two rotary joints with different axis of rotation to allow for natural foot movement such as plantar flexion, dorsiflexion, rotation, eversion and inversion. The preferred embodiment 30 includes such multiple joints with different axes of rotation. The composite shank 6c of composite footplate 6 is preferably integrated into footwear, such as a boot 32, with an external structure that allows for moments to be applied about the ankle joint in the direction of dorsiflexion and plantarflexion. The composite shank 6c can also be directly integrated into the sole of the shoe. For example, a carbon fiber composite shank 6c may be integrated into the heel of a boot, or the like. Alternatively, an integrated heel plate can also have extensions (not shown) that extend from the heel to the forefoot, allowing for large moments to be applied to the foot.

The composite shank 6c of the composite footplate 6 is preferably directly integrated into the sole of a shoe 32. The composite foot plate 6 transmits the forces developed by the actuator into the ground and foot 33 of the user. The functions of the foot plate 6 can be separated into two general functions, 1) interacting with the foot 33 and 2) interacting with the actuator of the exoskeleton 30.

Preferably, the composite foot plate 6 is directly integrated into the sole 34, between the rubber outsole that interfaces with the ground, and a soft foam sole 35 that separates the footplate 6 and foot 33. The footplate 6 must transmit actuator forces into the ground and into the foot 33 of the user, while remaining flexible and comfortable. This is achieved with a variable thickness carbon-fiber composite foot plate 6. The foot plate 6 is preferably approximately 3 mm thick under the heel of the foot 33, and thins out to about 1 mm under the toes. The thinning of the footplate 6 allows for toe flexion, while also storing and releasing elastic energy. Layers of unidirectional carbon fiber are laid up along the major axis of the foot 33 to provide strength. Outer layers of weaved carbon fiber are used for composite stability and to accommodate twisting loads.

The thickness of the footplate 6 may be adjusted to suite the application at hand. The footplate 6, particularly the composite shank portion 6c, should be as stiff as possible to efficiently transmit exoskeletal torque to the foot 33, but it must also be flexible enough to maintain natural foot range of motions. Current standard military boots, such as the McRae Hot Weather boots, are much stiffer than a typical standard civilian boot. This is partially due to a composite shank that is integrated into the sole. The composite shank provides rigid arch support and protects the foot 33 from repeated exposure to sharp items. Custom carbon fiber footplates are integrated into a lighter and more flexible tactical boot, such as the Rocky Elements of Service. The carbon fiber shank insert 6c of the present invention replaces the known composite shank and will provide many of the same functions as the composite shank in the McRae boot, while also interfacing with the exoskeleton 30, in accordance with the present invention. Thus, the exoskeleton 30 of the present invention can be easily incorporated into existing footwear 32.

Also, the second function of the composite foot plate, generally referred to as 6, is to connect and interact with the exoskeleton 30. The exoskeleton 30 includes the motor 1, electronics 15, drive spool 2 and lever 4, as discussed above. The vertical connector member 6b extends from a lateral side of the footplate shank 6c, under the heel. Vertical connector 6b also includes bearings for the dorsiflexion and plantarflexion. Therefore, the composite footplate 6 is preferably manufactured as a solid unitary member with a defined angle between the footplate 6c and vertical connector member 6b. Such angle may be modified as desired to suit given anatomy and provide optimal alignment. Custom composite footplates configurations can be provided to accommodate any single user.

Since the vertical connector member 6b includes a cylinder and socket joint connection, eversion and inversion movement are possible to provide and a degree of freedom to accommodate such eversion and inversion motion, as best seen in FIGS. 5A-5C. The ankle joint cross member 5 is also rigidly connected to the lever 4. This enables the motor 1 to drive the drive spool 2 to windup the drive belt 3 to, in turn, actuate the lever 4, causing the lever 4 and connected ankle joint cross 5 to plantarflex in accordance with the present invention. The plantarflexing ankle joint cross 5 then imparts these forces on the footplate 6c, while still allowing the footplate 6c to evert or invert. An articulated eversion/inversion joint adds some mass and complexity, but it allows for desirable free eversion/inversion motion and adapts to any user without imparting neutral-position forces. This articulated eversion/inversion joint also simplifies the geometry of the vertical connector member 6b, since it no longer needs to be flexible in the eversion/inversion direction. Furthermore, the lever arm 4 is integrated into/connected to the ankle joint cross member 5 and not into the composite footplate 6, simplifying the manufacturing process for the footplate. The eversion/inversion articulated joint can accommodate the complete range of motion achieved by the human ankle.

The articulate eversion/inversion enables the exoskeleton to be quickly discarded. The ankle joint cross 5 slides into the vertical connector member 6b and is then secured with a few set screws. The screws can be replaced with a locking feature, such as a thumb screw, a magnetic locking feature, or the like (not shown). Once the locking feature is disengaged, the foot plate portion 6 can be disengaged. Since the lever arm 4 and dorsiflexion/plantarflexion joint is no longer integrated into the composite foot plate 6, the foot plate 6 only differs from a regular boot in that it includes the vertical connector member 6b, which can be about 70 mm tall, 35 mm wide, 5 mm thick, and sits about 20 mm away from the lateral side of the foot. Shoes 32 with the composite footplate 6 only can be worn with minimal effect if the exoskeleton capability is not needed. Quickly disconnecting the upper portion of the exoskeleton 30 from the shoe, and leaving the foot plate 6 intact, could be valuable in situations where the operator needs to quickly remove the exoskeleton.

The exoskeleton 30 uses the electric motor 1, as in FIG. 4, and 201 of FIG. 7, to drive a unidirectional actuator. The motor is driven by a power source, such as a battery (not shown). This unidirectional actuator is an actuator that can apply forces or torques in one direction but exert little or no force or torque in the opposite direction. The unidirectional actuator of the present invention may only be unidirectional for a certain range of motion, if desired. The ankle drive belt 3, as shown in FIGS. 1-4, is one preferred embodiment of a unidirectional actuator because such a drive belt 3 can only pull when it is being wound onto the drive spool 2 and cannot push as it is being paid out from the drive spool 2. Other examples of unidirectional actuators (not shown) that may be employed with the present invention are winches, 5-bar linkage, Linkage with 5 or more bars, 4-bar linkage where one of the links is a string or cable, 5-bar linkage where one of the links is a string or cable, cam with an uncaptured follower, a rotary actuator with a slip clutch, a rotary actuator where mechanical feature interferes and transmit torque in one direction but do not interfere in the opposite direction, a linear actuator that pulls on a string or cable and a linear actuator that pushes on a mechanical feature without being connected, and the like. These alternatives are deemed to be within the scope of the present invention.

In accordance with the present invention, the drive belt 3 increases the range of unidirectionality, but is not required to be flexible. Furthermore, the drive belt 3 may be elastic in nature that stores energy in tension. While the motor 1 is shown with a direct drive of the drive spool 2 to take up the drive belt 3, a transmission may be used between the motor and spool as well. For example, during many activities, the human body exerts greater torques as the joint extends or flexes. A variable transmission can be used to increase the transmission ratio during angular regions that typically require greater levels of torque. In the case of an ankle exoskeleton, for example, linkage can be designed to have a higher transmission ratio as the ankle dorsiflexes. Various other transmissions may be used and still be within the scope of the present invention. These include a winch with variable radius spool, a timing belt pulley with variable radius, a chain and sprocket with variable radius and a cam and follower configuration.

Referring to FIGS. 5A-5C and 6A-6C, it can be seen that the exoskeleton 30 does not protrude from the anterior surface of the body. The embedded footplate 6 exerts forces beneath the heel of and against the ground next to the forefoot. As discussed above, belts and chains can be used in a manner similar to a winch. In the preferred embodiment 30 of the present invention, a drive 3 is employed. More specifically, the drive belt 3 is wrapped around the drive spool 2 which is driven by motor 1. The motor 1 applies tension to the drive belt 3 in a unidirectional manner, namely, when the drive belt 3 is being taken up about the drive spool. Furthermore, the radius of the drive spool 2 can be configured to achieve specific force profiles. These are just one of the many different configurations and mechanisms that may be used to carry out the present invention.

More specifically, the exoskeleton 30 of the present invention uses a unidirectional drive spool actuator where the drive spool 2 takes up the belt. While the drive spool 2 is preferably non-eccentric, it may be eccentrically configured instead. If an eccentric center of rotation of the drive spool is used, variable transmission ratios may be achieved beyond the change in transmission ratios as the wrapped drive belt 3 gets larger and smaller, if desired.

Figure 6A:
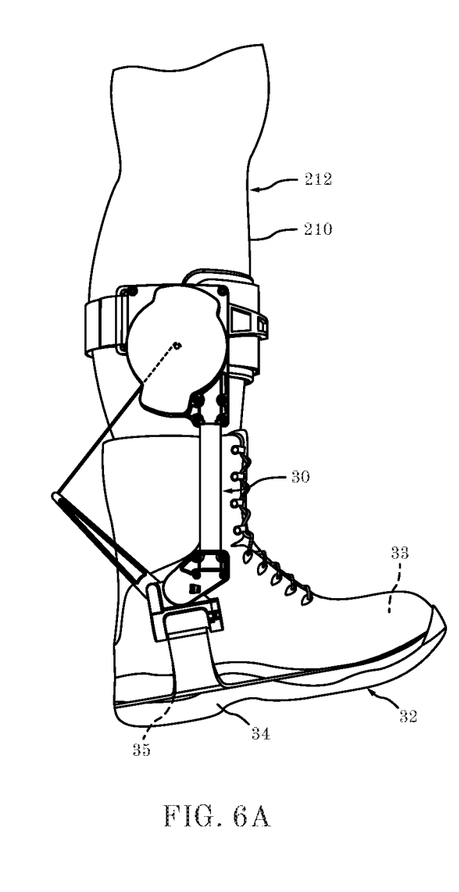
FIGS. 6A-C show front views of the exoskeleton device of the present invention with different degrees of dorsiflexion of the ankle joint.
Figure 6B:
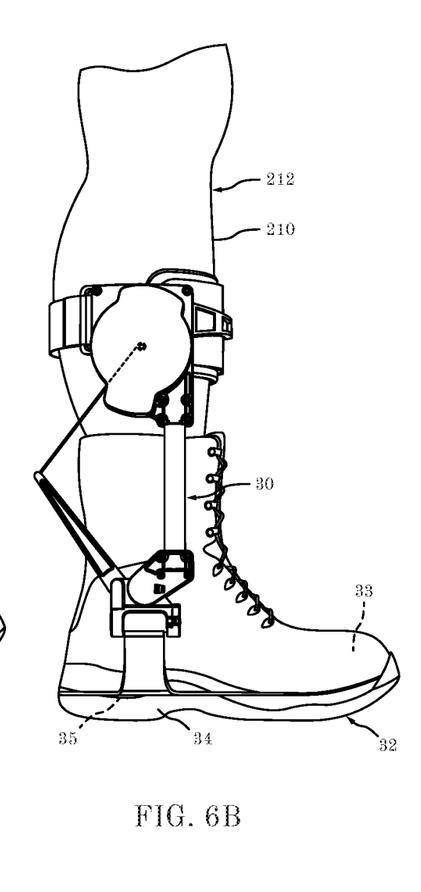
Figure 6C:
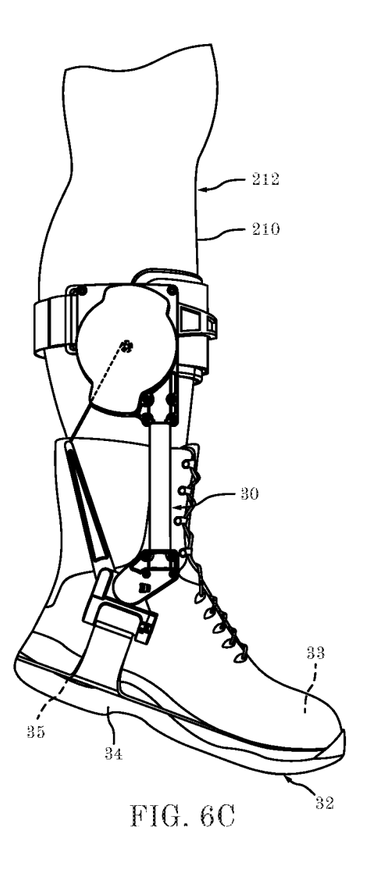

FIG. 6A shows a side view of the preferred embodiment of the exoskeleton 30 of the present invention. The actuator region of the lever arm 4 within with the lateral ankle joint bearing housing 25 and medial ankle joint bearing housing 26 is at the most extreme dorsiflexion angle. The drive belt 3 is pinned or rigidly connected to the drive spool 20. FIG. 6B shows a side view of the exoskeleton 30 of the present invention. The actuator is at a slight or no dorsiflexion angle. FIG. 6C a side view of the exoskeleton 30 with the exoskeleton 30 actuated a plantarflexion angle with the drive belt 3 partially wound about the drive spool 2. Since the drive belt 3 is pinned or rigidly connected to the drive spook 2, it can only apply a plantar flexion torque and is not able to apply a dorsiflexion torque. As a result of engagement of the motor 1, the drive belt 3 is wound about the drive spook to take up the drive belt 3. As the drive belt 3 winds around the drive spool 2, the transmission ratio can be configured to decrease upon rotation of the drive spool 2.

It should further be noted that FIG. 6A shows a side view of the exoskeleton 30 and boot 32 with the exoskeleton actuated is at the most extreme dorsiflexion angle. The unidirectional drive belt 3 is fixed to the variable radius drive spool 2 and can only apply tension forces. As the variable radius drive spool 2 rotates, the radius of the resultant spool increases, reducing the overall transmission ratio. The variable radius drive spool 2 is driven by the motor 1, which is preferably brushless. The unidirectional drive belt 3 is shown as a belt but it could also be a timing belt, a cord, series of parallel cords, flat fiber reinforced belt (fibers are surrounded by an abrasion resistant rubber such as urethane, polyurethane, silicone or neoprene, for example), flat steel belt or any other flexible structure that is capable of wrapping over small diameter spools, such as those less than 50 mm, and capable of withstanding high-tension forces, such as greater than 200 N. In FIG. 6B, the exoskeleton 30 and boot 32 are positioned at a neutral angle. FIG. 6C shows the exoskeleton at the most extreme plantarflexion angle.

Since a belt is used that winds around itself, the diameter of the overall spool increases, which reduces the transmission ratio. Therefore, reducing the thickness of the belt also reduces the effect on the transmission ratio, but it also generally reduces the strength of the belt. Thus, reducing the transmission ratio as the device plantarflexes may improve efficiency since the peak torque occurs during maximum dorsiflexion and decreases during plantarflexion.

In general, the motor 1 may be directly connected to the drive spool 3 or first connected to a reduction transmission such as a gear transmission, pulley transmission, timing belt transmission, cycloid transmission, friction transmission, or harmonic transmission. While any type of motor may be used with the present invention it is preferred that a custom motor 1 be used, such as a D8.0 motor with the FlexSEA-Rigid electronics. The custom D8.0 motor has a thickness in the range of 17.2 mm, which is well suited for use with the present invention. Furthermore, it includes features that reduces the length of the drive spool 2 and the thickness of the electronics 15. The D8.0 motor has increased power density of the actuator to limit the lateral protrusion of the device, which is particularly advantageous for the present exoskeleton 30. The axis of the motor 1 is notably perpendicular to the major axis of the leg and perpendicular to the sagittal plane. Electronics, such as FlexSEA-Rigid electronics, are attached to the lateral side of the motor 1.

In use, the motor 1 is powered and controlled by the onboard control electronics 15 and a battery (not shown). Angle of the motor 1 is measured with the motor angle sensor 16, 17 and the angle of the ankle output joint is preferably measured with a separate angle joint sensor 7, 8. The sensor can be any type of sensor, such as an optical encoder, magnetic angle sensor, hall effect sensor, potentiometer, capacitive sensor, inductive sensor, or a linear variable differential transformer (LVDT).

The motor angle sensor 16, 17 and ankle angle sensor 7, 8 are preferably related when the actuator is engaged and exerting torque, but independent when the actuator is not engaged. Thus, during operation, the control electronics 15 controls the take up and pay of the drive belt about the drive spool. The different components of the exoskeleton 30 are electronically interconnected to the control electronics 15 so they may be controlled and monitored as required. For example, the sensors, motor 1 and power supply, such as a battery (not shown), are electronically connected to the control electronics 15 whereby the timing of such take up and pay out of the drive belt 3 via the motor 1 can be timed or synchronized to the gait of the user, with the assistance of the sensors, so that the plantar flexion torque can be applied by the exoskeleton at the appropriate time to use the work created by that torque to assist in the plantar flexion of the joint to, in turn, facilitate walking.

For example, the control electronics 15 can be programmed to carry out different tasks, such as inertial sensor readings, clock synchronization between the microcontrollers, serial and PC communication, non-volatile memory interface, and the like. These features enable better high-level controllers. For example, a 168 MHz Cortex-M4F STM32F427 controller may be used to carry out computing cycles available for executing high-level algorithms concerning control of the exoskeleton 30. Field Programmable Gate Arrays (FPGA), Complex Programmable Logic Devices (CPLD), Application Specific Integrated Circuits (ASIC), and Graphical Processing Units (GPU) may also be used for hardware math acceleration and control. This makes it also possible to use machine learning techniques in real time.

The described exoskeleton can be worn on one leg or both legs. When the exoskeleton is worn in a bilateral configuration, the two exoskeletons can communicate with wires or wireless communication protocols to share state information for purposes of control and telemetry.

It would be appreciated by those skilled in the art that various changes and modifications can be made to the illustrated embodiments without departing from the spirit of the present invention. All such modifications and changes are intended to be covered by the appended claims.

What is claimed is:

1. A composite foot plate for footwear, comprising:
   a footplate integrated into a sole of the footwear;
   an outer sole located between the footplate and ground;
   an inner sole located above the footplate;
   the footplate extending upward only from one lateral most side surface of the footwear;
   the footplate being made of composite material with fibers in a plurality of orientations and is flexible at a metatarsal joint region;
   the footplate being varied in thickness, and
   a mechanical joint disposed on the footplate, the mechanical joint is configured and arranged for plantar flexion, dorsiflexion, eversion and inversion of the footplate relative to a shank of a user.

2. The composite foot plate for footwear of claim 1, wherein the mechanical joint includes an upstanding portion which is flexible to allow for misalignment and eversion/inversion.

3. The composite foot plate for footwear of claim 2, wherein the upstanding portion includes a lever arm that interacts with an exoskeleton actuator.

4. The composite foot plate for footwear of claim 1, wherein the mechanical joint includes
   a first joint with an axis of rotation configured to be perpendicular to a sagittal plane of the user, and
   a second joint with an axis of rotation configured to be perpendicular to the axis of rotation of the first joint.

5. The composite foot plate for footwear of claim 4,
   wherein the mechanical joint includes an upstanding portion which is flexible to allow for misalignment and eversion/inversion, and
   wherein the upstanding portion includes a lever arm that interacts with an exoskeleton actuator.

6. The composite foot plate for footwear of claim 1, wherein the footplate is made of a material selected from the group consisting of unidirectional carbon fiber, twill weave carbon fiber, and/or plain weave carbon fiber.

7. The composite foot plate for footwear of claim 1, wherein the footplate further includes embedded sensors selected from the group consisting of force sensors, pressure sensors, strain sensors, IMU sensor, humidity or liquid sensor, and temperature sensors.

8. A composite foot plate for footwear, comprising:
   a footplate integrated into a sole of the footwear;
   an outer sole located between the footplate and ground;
   an inner sole located above the footplate;
   the footplate extending upward on the lateral side of the footwear;
   the footplate being made of composite material with fibers in a plurality of orientations and is flexible at a metatarsal joint region;
   the footplate being varied in thickness, and
   a mechanical joint disposed on the footplate, the mechanical joint is configured and arranged for plantar flexion, dorsiflexion, eversion and inversion of the footplate relative to a shank of a user, the-mechanical joint includes,
   an ankle dorsiflexion/planar-flexion joint with an axis of rotation configured to be perpendicular to a sagittal plane of the user, and
   an ankle eversion/inversion joint with an axis of rotation configured to be perpendicular to the axis of rotation of the first joint,
   wherein the ankle eversion/inversion joint is proximal the sole of the footwear and the ankle dorsiflexion/planar-flexion joint is proximal to the ankle eversion/inversion joint.

9. The composite foot plate for footwear of claim 8, wherein the-mechanical joint includes an upstanding portion which is flexible to allow for misalignment and eversion/inversion.

10. The composite foot plate for footwear of claim 9, wherein the upstanding portion includes a lever arm that interacts with an exoskeleton actuator.

11. The composite foot plate for footwear of claim 8, wherein the footplate is made of a material selected from the group consisting of unidirectional carbon fiber, twill weave carbon fiber, and/or plain weave carbon fiber.

12. The composite foot plate for footwear of claim 8, wherein the footplate further includes embedded sensors selected from the group consisting of force sensors, pressure sensors, strain sensors, IMU sensor, humidity or liquid sensor, and temperature sensors.

13. The composite foot plate for footwear of claim 8,
wherein the mechanical joint includes an upstanding portion which is flexible to allow for misalignment and eversion/inversion, and
wherein the upstanding portion includes a lever arm that interacts with an exoskeleton actuator.

\* \* \* \* \*